(12) United States Patent
Arkossy et al.

(10) Patent No.: US 11,617,872 B2
(45) Date of Patent: Apr. 4, 2023

(54) APPARATUS AND METHOD FOR ESTABLISHING AND/OR RELEASING A MEDICAL THREADED CONNECTION THROUGH WHICH A FLUID CAN FLOW

(71) Applicant: FRESENIUS MEDICAL CARE DEUTSCHLAND GMBH, Bad Homburg (DE)

(72) Inventors: Otto Arkossy, Budapest (HU); Pia Daniel, Bodman (DE); Christopher Hauke, Mainz-Kostheim (DE); Pascal Kopperschmidt, Dittelbrunn (DE); Kai-Uwe Ritter, Rednitz-Hembach (DE); Cacilia Scholz, Schwalbach (DE); Elke Schulte, Schweinfurt (DE); Reiner Spickermann, Wasserlosen-Burghausen (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 820 days.

(21) Appl. No.: 16/479,935

(22) PCT Filed: Jan. 29, 2018

(86) PCT No.: PCT/EP2018/052117
§ 371 (c)(1),
(2) Date: Jul. 23, 2019

(87) PCT Pub. No.: WO2018/138327
PCT Pub. Date: Aug. 2, 2018

(65) Prior Publication Data
US 2019/0381302 A1  Dec. 19, 2019

(30) Foreign Application Priority Data
Jan. 30, 2017  (DE) .................... 10 2017 201 447.4

(51) Int. Cl.
*B23P 19/06* (2006.01)
*A61M 39/18* (2006.01)
(Continued)

(52) U.S. Cl.
CPC .......... *A61M 39/10* (2013.01); *A61M 1/3661* (2014.02); *A61M 39/18* (2013.01);
(Continued)

(58) Field of Classification Search
CPC .............. A61M 39/18; A61M 2207/00; A61M 2207/10; A61M 39/10; A61M 2039/1033;
(Continued)

(56) References Cited

U.S. PATENT DOCUMENTS

| 4,845,827 A | 7/1989 | Vandermast et al. |
| 7,024,968 B2 | 4/2006 | Raudabough et al. |

(Continued)

FOREIGN PATENT DOCUMENTS

| CN | 1694654 A | 11/2005 |
| CN | 1942216 A | 4/2007 |

(Continued)

OTHER PUBLICATIONS

Translation of JPH08725A (Year: 1996).*
(Continued)

*Primary Examiner* — Matthew P Travers
(74) *Attorney, Agent, or Firm* — Kilyk & Bowersox, P.L.L.C.

(57) ABSTRACT

An apparatus is provided for producing and/or disengaging a fluid flow-capable medical threaded connection. The connection can be a Luer lock connection. The apparatus includes a first receiving device for receiving a first connecting element, and a second receiving device for receiving a second connecting element. The first receiving device and the second receiving device are rotatable relative to each (Continued)

Figure 1A:
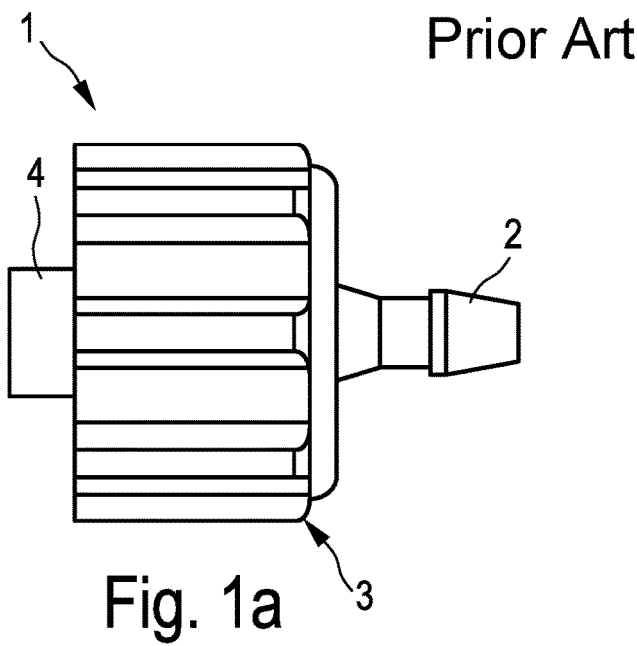

other about a common screwing axis, and displaceable relative to each other along the screwing axis. The apparatus is designed to relatively move the first receiving device and the second receiving device toward and away from each other such that the first connecting element and the second connecting element can be screwed together or disengaged. An associated connecting element can be introduced into the first receiving device and/or into the second receiving device, in a radial direction relative to the screwing axis. A method is also provided.

12 Claims, 6 Drawing Sheets

(51) Int. Cl.
*A61M 39/10* (2006.01)
*A61M 1/36* (2006.01)

(52) U.S. Cl.
CPC .... *B23P 19/061* (2013.01); *A61M 2039/1016* (2013.01); *A61M 2039/1033* (2013.01); *A61M 2205/3327* (2013.01); *A61M 2207/00* (2013.01); *A61M 2207/10* (2013.01)

(58) Field of Classification Search
CPC .. A61M 2039/1038; A61M 2039/1083; A61M 2039/1088; B23P 19/06; B23P 19/061
See application file for complete search history.

(56) References Cited

U.S. PATENT DOCUMENTS

| | | | |
|---|---|---|---|
| 2004/0211484 A1 | 10/2004 | Fournie et al. | |
| 2005/0224405 A1 | 10/2005 | Neri et al. | |
| 2005/0271465 A1 | 12/2005 | Lehmann | |
| 2006/0035494 A1* | 2/2006 | Sugaya | A61M 39/18 439/157 |
| 2007/0073215 A1* | 3/2007 | Wieslander | A61M 39/18 604/29 |
| 2008/0140014 A1 | 6/2008 | Miller et al. | |
| 2008/0287859 A1 | 11/2008 | Miller et al. | |
| 2009/0012451 A1 | 1/2009 | Sobue et al. | |
| 2012/0209168 A1 | 8/2012 | Katsuyoshi et al. | |
| 2015/0065916 A1 | 3/2015 | Maguire et al. | |
| 2016/0249990 A1 | 9/2016 | Glozman et al. | |
| 2019/0009072 A1 | 1/2019 | Schedler et al. | |

FOREIGN PATENT DOCUMENTS

| | | |
|---|---|---|
| CN | 101031327 A | 9/2007 |
| CN | 101360526 A | 2/2009 |
| CN | 104129567 A | 11/2014 |
| EP | 0256640 A2 | 2/1988 |
| EP | 0441628 A2 | 8/1991 |
| EP | 2799100 A2 | 5/2014 |
| EP | 2756863 A2 | 7/2014 |
| JP | 8-725 A | 1/1996 |
| JP | 11-253553 A | 9/1999 |
| WO | 8402849 | 8/1984 |
| WO | 2004047883 A2 | 6/2004 |
| WO | 2005000378 A2 | 1/2005 |
| WO | 2006041442 A1 | 4/2006 |
| WO | 2010029521 A2 | 3/2010 |

OTHER PUBLICATIONS

Office Action issued in corresponding Japanese Patent Application No. 2019-541126 dated Oct. 13, 2021 (5 pages).
International Preliminary Report on Patentability issued in corresponding International Patent Application No. PCT/EP2018/052117 dated Aug. 8, 2019 (8 pages).
Office Action issued in corresponding Chinese Patent Application No. 201880009219.4 dated Jan. 11, 2022 (English translation only)(8 pages).
International Search Report and Written Opinion issued in corresponding International Patent Application No. PCT/EP2018/052117 (with English translation of International Search Report) dated Apr. 10, 2018 (11 pages).
Office Action issued in corresponding Chinese Patent Application No. 201880009219.4 dated Apr. 25, 2021 (English translation only)(4 pages).
Office Action issued in corresponding Chinese Patent Application No. 201880009219.4 dated Jun. 2, 2022 (with English translation)(18 pages).

* cited by examiner

Prior Art

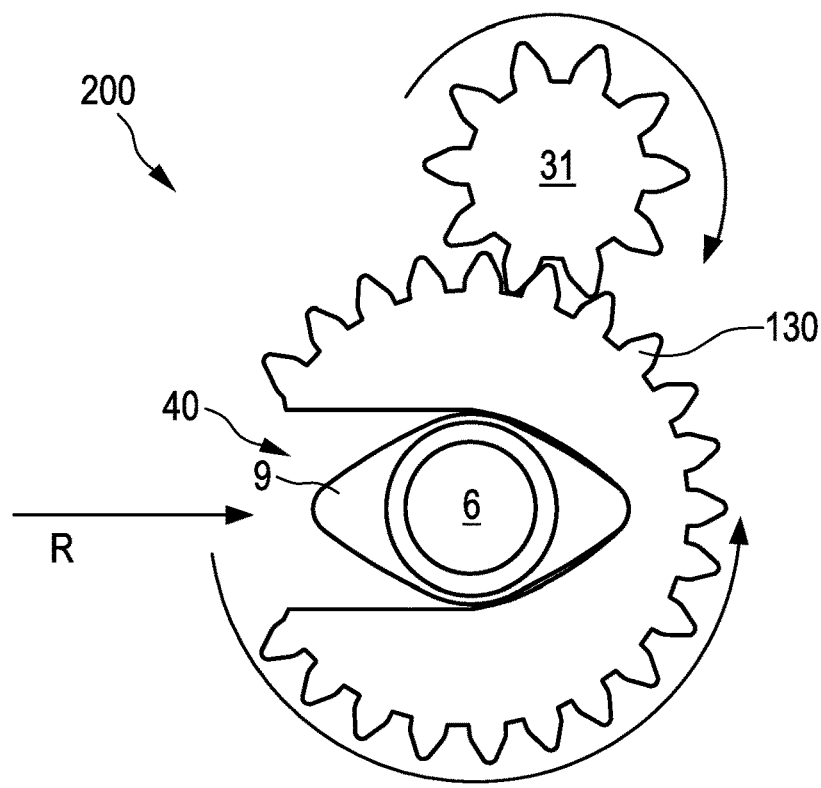
Fig. 7
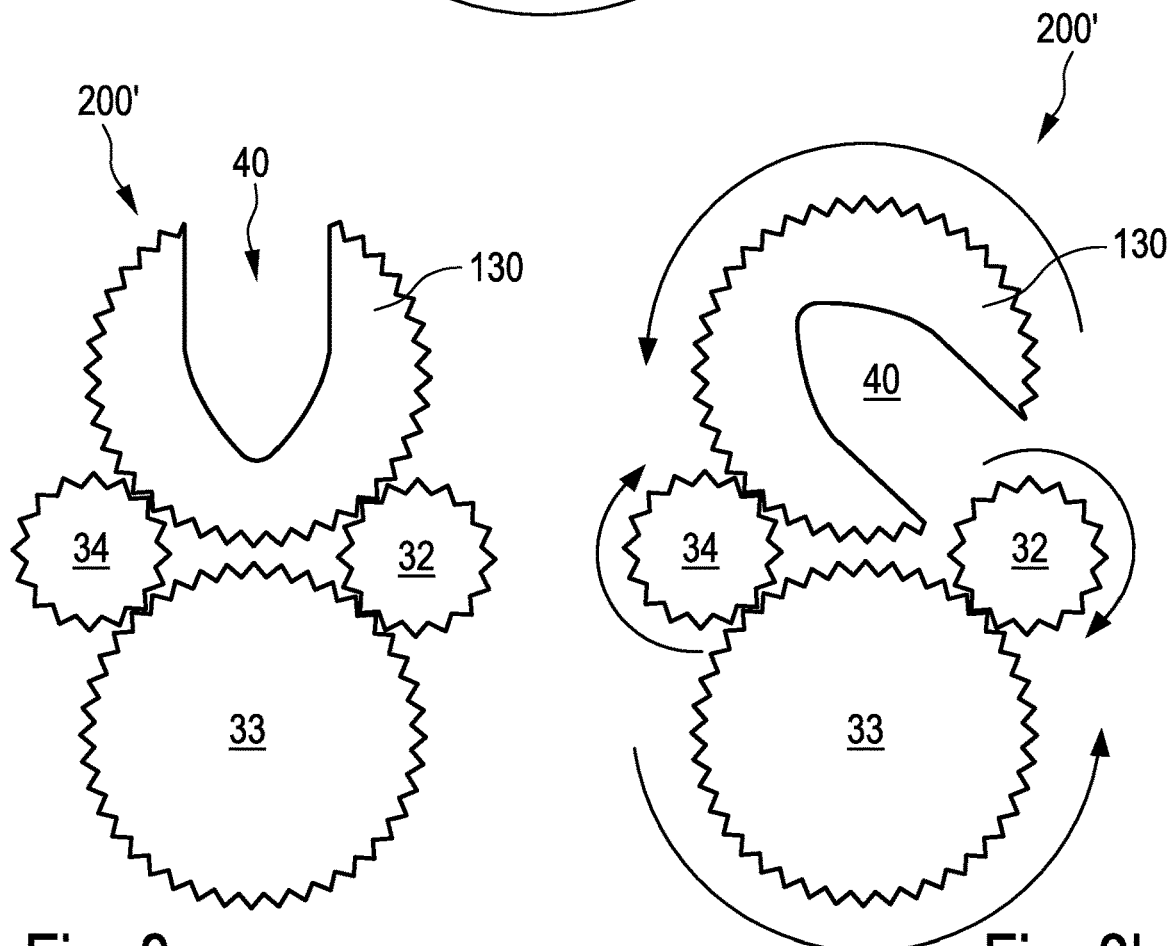
Fig. 8a
Fig. 8b

APPARATUS AND METHOD FOR ESTABLISHING AND/OR RELEASING A MEDICAL THREADED CONNECTION THROUGH WHICH A FLUID CAN FLOW

This application is a National Stage Application of PCT/EP2018/052117, filed Jan. 29, 2018, which claims priority to German Patent Application No. 10 2017 201 447.4, filed Jan. 30, 2017.

The invention relates to an apparatus for producing and/or disengaging a fluid flow-capable medical threaded connection of a first connecting element and a second connecting element, in particular for producing and/or disengaging a Luer lock connection, wherein the apparatus comprises a first receiving device for receiving the first connecting element and a second receiving device for receiving the second connecting element, wherein the first receiving device and the second receiving device are rotatable relative to each other about a common screwing axis and displaceable relative to each other along said screwing axis, and wherein the apparatus is designed to relatively move the first receiving device and the second receiving device toward each other after the introduction of the first connecting element into the first receiving device and the introduction of the second connecting element into the second receiving device such that the first connecting element and the second connecting element are screwed together or the threaded connection is disengaged.

Establishing vascular access for administering medication and/or establishing a fluid connection between a patient's blood circulation and an external fluid system is necessary in the medical treatment of many patients. In particular with respect to venipuncturing blood vessels, so-called "cannulas" are used.

Cannulas are generally hollow needles, normally comprising an applicably designed tip at its end for the intended purpose, in particular a tip specially ground for the respective intended application, often a very sharp and pointed tip, usually a facet-cut tip or a lancet-cut tip in the case of injection needles, and normally a respective connecting element at its other end for creating a fluid connection to the rest of the external fluid system, a syringe, a dosing chamber, a medical instrument or the like. With most cannulas, the connecting element is thereby a so-called Luer-type connector or a so-called Luer lock connector which is connectable to a correspondingly designed suitable counterpart, wherein the counterpart to a Luer-type connector is a correspondingly designed Luer-type connector and the suitable counterpart to a Luer lock connector is a correspondingly designed Luer lock connector.

A threaded Luer-type connection, which usually comprises a male Luer connector as well as a female Luer connector, are generally known from the prior art. In particular, widely diverse embodiments of Luer connectors having a male and/or female Luer-type connecting section are known, e.g. from DE 10 2015 211 370 B3, differing in particular in terms of their outer contour as well as additionally provided connections.

Threaded Luer-type connections are standardized internationally in the ISO 594 standard, throughout Europe in the EN 205953 (respectively EN 1707) standard, and in Germany by the DIN EN 20594 standard. The use of threaded Luer connections enables producing manufacturer-independent, safe, sealed and sterile connections, as are particularly imperative in medical technology. Standardization-compliant standard Luer connectors from different manufacturers can thereby be freely combined with one another. Thus, syringes and cannulas from different manufacturers can be combined in producing a threaded Luer-type connection.

A male Luer-type connector thereby has a tubular body enclosing a lumen with a conical outer sheath, wherein the conical outer sheath exhibits a 6% angle of slope from the tip to the base in accordance with the standard.

A female Luer-type connector has a hollow accommodating body, configured to correspond to the conical outer sheath of the male Luer connector, with a conical, sleeve-shaped receiver and likewise a 6% angle of slope. A collar, often protruding radially outwardly, is further provided at the outer end of the female Luer connector. Given the suitably selected size, the female Luer connector can be easily fit onto the male Luer connector, wherein the female Luer connector can be securely held on the male Luer connector by frictional locking and provides a fluid-tight connection with the male Luer connector. However, as easily as the female Luer-type connector can be connected to the male Luer-type connector, the connection can be just as easily separated again.

For this reason, in addition to the usual Luer-type connections, so-called threaded Luer lock connections have also been developed, these likewise being generally known from the prior art. These additionally exhibit an internal thread on the male Luer connector into which the radially protruding locking elements, in particular an external thread of a correspondingly designed female Luer lock connector, can be inserted, via which the female Luer lock connector can be screwed to the male Luer lock connector so as to connect the male Luer lock connector and the female Luer lock connector together at high tensile strength, at least within certain limits.

Female Luer connectors or female Luer lock connectors are usually situated on a cannula or a catheter or at the inlet of a line. Male Luer connectors or male Luer lock connectors are mostly situated on a syringe, a dosing chamber, a medical instrument or at the outlet of a line.

Generally speaking, all fluid connections between a patient and an external fluid system, a syringe, a dosing container, a medical instrument or the like as well as often a plurality of fluid connections within the external fluid system fluidly connected to the patient are Luer-type connections or Luer lock connections.

Particularly in the case of patients with a chronic illness where their treatment requires regularly repeated vasculature cannulation, it is important to keep the mechanical stress of puncturing a blood vessel, also referred to as "cannulation," as low as possible and to be as gentle as possible on the vessel to be punctured during the cannulation.

Not only does cannulation itself thereby represent stress for the relative vessels but in fact any mechanical stressing of the vessels does, in particular especially movement of cannulas already inserted into a vessel. This means that particularly during the connecting procedure; i.e. when connecting the cannula to the rest of the external fluid system, a syringe or a dosing chamber, a medical instrument or the like, which generally occurs during cannulation, there is the risk of subjecting the vessel to more stress than necessary or even damaging it.

Furthermore, it is important with respect to the patient for the fluid connection between the cannula and other components connected to the cannula as well as, particularly in the case of an external fluid system, all the fluid connections of the fluid system, to be securely sealed, because the unintentional disengaging of a fluid connection, for example between a cannula and an infusion tube due to an improper connection can have life-threatening consequences.

For the aforementioned reasons, it appears advantageous for an apparatus to be provided with which medical fluid connections, in particular Luer lock connections, can be automated and produced autonomously.

Using an apparatus to make a Luer lock connection is in general known from the prior part, in particular from WO 2004/047883 A2. However, the apparatus described in WO 2004/047883 A2 relates to a manually operable apparatus, in particular an apparatus used in conjunction with a so-called "autoinjector." Autoinjectors are apparatus used in particular with patients who inject themselves, for example diabetes patients with insulin doses or emergency adrenalin injections in cases of allergic shock.

The present invention is based on the task of providing an improved apparatus for producing and/or disengaging a fluid flow-capable medical threaded connection of a first connecting element and a second connecting element, in particular an apparatus by means of which the producing and/or disengaging of a fluid flow-capable medical threaded connection can be automated.

Serving to solve this task is an apparatus for producing and/or disengaging a fluid flow-capable medical threaded connection in accordance with claim 1 as well as method for producing and/or disengaging a fluid flow-capable medical threaded connection. Preferential configurations of the invention constitute the subject matter of the subclaims and the present description of the invention.

An apparatus according to the invention for producing and/or disengaging a fluid flow-capable medical threaded connection of a first connecting element and a second connecting element, in particular for producing and/or disengaging a Luer lock connection, comprises a first receiving device for receiving the first connecting element and a second receiving device for receiving the second connecting element, wherein the first receiving device and the second receiving device are rotatable relative to each other about a common screwing axis and displaceable relative to each other along said screwing axis. The apparatus is thereby designed to relatively move the first receiving device and the second receiving device toward each other after the introduction of the first connecting element into the first receiving device and the introduction of the second connecting element into the second receiving device such that the first connecting element and the second connecting element are screwed together or the threaded connection is disengaged.

One feature of an inventive apparatus is in particular that the associated connecting element can be introduced into the first receiving device and/or the second receiving device in the radial direction relative to the screwing axis.

Because at least one connecting element required to create the threaded connection can be introduced radially into the respectively associated receiving device relative to the screwing axis in an inventive apparatus for producing and/or disengaging a medical threaded connection, an inventive apparatus makes it particularly simple to produce a medical threaded connection of a first connecting element and a second connecting element, in which at least one of the connecting elements comprises a tube or is connected to a tube, because in the case of connecting elements comprising a tube or connected to a tube, it is clearly more simple, and thus also clearly more advantageous, for at least one connecting element to be radially introduced versus axially introduced.

In particular, all the threaded connections of an external fluid system can be securely and repeatably made by means of an apparatus according to the invention.

A threaded connection in the sense of the invention is thereby a connection made by screwing an internal thread to an external thread.

A medical threaded connection is thereby a threaded connection suited for use in medical applications, in particular a threaded connection made with sterilizable material. A fluid flow-capable threaded connection is a threaded connection through which a fluid can flow; in the case of a medical threaded connection, in particular a medication in liquid form and/or a bodily fluid and/or a gas, wherein the threaded connection is in this case preferably designed to be gas-tight and/or liquid-tight.

Termed a screwing axis in the sense of the invention is thereby that axis about which the first connecting element and the second connecting element rotate relative to each other to create and/or disengage the threaded connection.

Preferably, an apparatus according to the invention is designed such that the first connecting element and/or the second connecting element can be introduced into the respectively associated receiving device in the radial direction relative to the screwing axis. In some cases, however, it can also be advantageous for the first connecting element and/or second connecting element to be radially slid, in particular inserted, into the respectively associated receiving device.

Preferably, an apparatus according to the invention is further designed such that the first connecting element and/or the second connecting element can be manually and/or automatically introduced into the respectively associated receiving device. For automated introduction of the first connecting element and/or the second connecting element into the apparatus, in particular into the first receiving device and/or into the second receiving device, the apparatus is preferably designed such that the first connecting element and/or the second connecting element can be guided along the simplest trajectory possible when being introduced.

The two receiving devices of an inventive apparatus; i.e. the first receiving device and the second receiving device, can preferably move translationally in the axial direction along the common screwing axis relative to one another and are in particular rotatable about the screwing axis relative to each other.

To create the threaded connection, it is particularly preferential for the first receiving device and the second receiving device to initially be brought together axially, in particular pressed together, preferably at least brought into contact, in order to then subsequently be able to be rotated around the screwing axis relative to one another, in particular by the applying of a defined axial force, particularly by the applying of a compressive axial force.

To disengage a threaded connection, the first receiving device and the second receiving device can preferably be initially rotated about the screwing axis relative to each other in a first step, in particular under application of an axial force acting to pull them apart, in order to then, in a further step, be able to be moved translationally in the axial direction along the screwing axis relative to one another, in particular apart.

Preferentially, an inventive apparatus is designed such that, both in the first receiving device and in the second receiving device, the respectively associated connecting element can be introduced in the radial direction relative to the screwing axis. Threaded connections can thereby be made in a particularly simple manner with an inventive apparatus in which both of the connecting elements respectively comprise a tube or are connected to a tube.

Preferentially, to receive the associated connecting element, the first receiving device and/or the second receiving device comprise(s) a correspondingly designed recess, which is outwardly open in the radial direction, or a gripper. In other words, alternatively, in particular instead of a receiving device having a recess outwardly open in the radial direction, at least one receiving device of an inventive apparatus can also comprise a gripper or be designed as a gripper.

A recess which is outwardly open in the radial direction, likewise in relation to the screwing axis, enables particularly simple providing of a receiving device into which an associated connecting element can be radially introduced, in particular without a great degree of control required.

In order to be able to receive many different connecting elements and thus be able to be used in producing and/or disengaging as many different threaded connections as possible, the first receiving device and/or the second receiving device of an inventive apparatus preferably comprise(s) one or more exchangeable receiving inserts and/or one or more exchangeable grippers. This thereby significantly increases the flexibility of the apparatus in simple manner.

In one advantageous configuration of an apparatus according to the invention, the first receiving device and/or the second receiving device is/are designed to receive the associated connecting element in torsion-fixed manner in relation to rotation about the screwing axis. In other words, that means that in an advantageous configuration of an inventive apparatus, at least one of the two receiving devices is designed to receive the associated connecting element in a manner secured against twisting around the screwing axis. Preferably, the first receiving device and/or the second receiving device is/are thereby designed to secure an associated connecting element inserted into the receiving device against rotation by form-fit; i.e. positive locking.

This can for example be achieved by the receiving device having, at least in one region, an inner contour adapted to the outer counter of the connecting element, which is designed so as to prevent rotation around the screwing axis.

For example, if a connecting element to be received has a hexagonal outer contour, positive anti-rotation locking can be easily produced by a correspondingly designed hexagonal inner contour. Further geometries to a connecting element to be received can also be used to create positive anti-rotation locking, for example the so-called "wings" frequently utilized in Luer lock connectors having female connecting sections or axially running ribs protruding outward in the radial direction arranged on a connecting element, which can produce a form-fit secured against rotation, for example in combination with a pin or bar projecting radially inwardly into the recess.

Alternatively or additionally, the receiving device can also comprise an anti-rotation element, in particular an active or passive anti-rotation element, by means of which the connecting element can be secured against rotation about the screwing axis at least subsequent to the connecting element being introduced into the receiving device.

This can for example be achieved by means of an anti-rotation pin projecting radially inwardly into the receiving device, wherein the anti-rotation element can also be designed as an active, preferably radially inwardly retractable, anti-rotation element, and not operatively connected to the introduced connecting element until after said connecting element has been introduced.

Alternatively or additionally, the connecting element can also be secured against rotation in the receiving device by force-fit, or friction-fit respectively, whereby preferably at least one of the receiving devices comprises a tensioning device thereto, in particular a tensible clamping device.

Preferably, the first connecting element and the second connecting element can in each case be axially fixed in the associated receiving device in an apparatus according to invention.

In a further advantageous configuration of an apparatus according to the invention, the apparatus is designed to at least semi-automatically produce and/or disengage the threaded connection. The inventive apparatus is thereby designed in particular to automatically screw the two connecting elements together and/or automatically disengage the connection of the threaded connection, wherein the apparatus preferably comprises a control device thereto, in particular a control device having a sensor device and/or an actuator device. The control device is preferably part of a cannulation robot, in particular part of the control device of the cannulation robot, by means of which particularly the automatic cannulation of a patient's blood vessel is controlled.

Particularly preferentially, an apparatus according to the invention is designed to be used together with a so-called cannulation robot having at least one receiving device for receiving a cannula, wherein preferably the receiving device of the cannulation robot, by means of which the cannula is received, held and/or guided during cannulation, forms a receiving device of the inventive apparatus, in particular the first receiving device.

Cannulation robots are generally known in the prior art, for example from US 2015/0065916 A1, WO 2015/052719 A1 and WO 2010/029521 A2, to which reference is hereby made for further details on cannulation robots. Cannulation robots are usually designed to autonomously prepare a patient cannulation procedure and autonomously perform the cannulation using suitable sensor technology and motor function.

Preferably, an apparatus according to the invention is designed to make a threaded connection between a first connecting element and a second connecting element after a cannulation procedure, wherein an inventive apparatus can preferably screw the cannula as the first connecting element to a second connecting element, preferably a tube connector or the like.

When an inventive apparatus is designed to produce a threaded connection between a cannula and a further connecting element after a cannulation procedure, the threaded connection can preferably be made immediately after the cannulation procedure, in particular prior to the receiving device of the cannulation robot releasing the cannula, whereby the receiving device of the cannulation robot with which the cannula is held is in this case preferably used as the receiving device, in particular as the first receiving device. Doing so can thus avoid multiple handling of the cannula already inside the patient and thereby keep the mechanical stressing of the vessel venipunctured by the cannula as low as possible.

On the other hand, an inventive apparatus is preferably further designed to produce and/or disengage a threaded connection independently of a cannulation procedure. In particular, an inventive apparatus is preferably designed to produce and/or disengage one or more threaded connections of an external fluid system fluidly connectable to a patient independent of a cannulation procedure, in particular beforehand; i.e. not on the patient.

An inventive apparatus thus enables the particularly simple producing and/or disengaging of the threaded connections of a fluid system, in particular of medical threaded connections, in particular tube connections, whereby the threaded connections can be automated and thus be produced in particularly secure and repeatable manner, and in particular, largely without damage.

In some cases, it can be advantageous for not only the screwing as such to be able to be automated by means of an inventive apparatus and/or the disengaging of the threaded connection as such, but also the introducing of the first connecting element and/or the second connecting element and/or the furnishing of the first connecting element and/or second connecting element to be able to be automated.

When an inventive apparatus comprises a sensor device, same preferably relates to a torque sensor apparatus and/or an axial force measuring apparatus.

A sensor apparatus enables particularly precise controlling of an inventive apparatus and, as a result, threaded connections can be made and/or disengaged in particularly repeatable manner; in particular, particularly reliably secure threaded connections can thereby be made since particularly damage to the threaded connection due to excessive torque and/or excessive axial force being applied can thereby be readily ascertained.

Alternatively or additionally, instead of a prespecified force and/or torque-controlled producing of the threaded connection, or respectively a force and/or torque-controlled disengaging of the threaded connection, the apparatus according to the invention enables the threaded connection to also be produced and/or disengaged under rotational angle and/or path of displacement control, in particular regulation.

To that end, an inventive apparatus preferably comprises an angle measuring apparatus for detecting the relative angle traveled and/or a distance measuring apparatus for detecting the axial distance traveled along the screwing axis by the first receiving device and/or the second receiving device, in particular to detect the relative distance travelled.

By means of a suitably designed sensor apparatus and a correspondingly designed control apparatus, not only can threaded connections be repeatably disengaged or established but it also becomes particularly simple to monitor the producing and/or disengaging of the connections. In particular, this enables determining whether the first connecting element and the second connecting element are properly screwed together or the threaded connection fully disengaged, whereby preferably a setpoint specification is compared to an actual specification to that end, in particular a target torque to an actual torque value.

To protect the threaded connection from damage, it is additionally advantageous for the apparatus to be designed such that the relative movement between the first receiving device and the second receiving device is stopped upon the exceeding of a prespecified threshold. Alternatively, a target current curve of a drive motor can also be determined and be in particular compared to an actual current curve, and the drive motor switched off particularly upon the exceeding of a defined threshold. A particularly simple overload protection to protect the threaded connection can thereby be provided and damage to the threaded connection prevented in particularly simply and effective manner.

An alternative option for realizing overload protection and/or providing tolerance compensation consists of providing the inventive apparatus with a spring element and/or a damping element, which is preferably arranged in a bypass load path, wherein an inventive apparatus in this case is preferably designed—after a defined, maximum permissible axial force has been exceeded and/or a defined torque has been exceeded—to divert a (further) generated axial force and/or a (further) generated torque to the spring element and/or the damping element via the bypass load path and not further transmit same to the threaded connection, whereby the threaded connection can be protected against overload, in particular mechanical overload.

In a further advantageous configuration of an inventive apparatus, one of the two receiving devices, in particular the first receiving device, is designed for receiving a first connecting element comprising a first connecting section having a sleeve-shaped internal thread arranged concentric to a first axis, in particular for receiving a first connecting element with a male Luer lock connecting section, while the other receiving device, in particular the second receiving device, is designed for receiving a second connecting element comprising a second connecting section having an external thread arranged concentric to a second axis, in particular for receiving a second connecting element with a female Luer lock connecting section.

Due to the routine use of connecting elements with Luer lock connecting sections, in particular in the medical field, a broad field of application thus results for an accordingly designed inventive apparatus.

In a further advantageous configuration of an inventive apparatus, the apparatus is designed such that the first axis of the first connecting element and the second axis of the second connecting element are aligned along the screwing axis or can be aligned along the screwing axis after the first connecting element being introduced into the first receiving device and after the second connecting element being introduced into the second in receiving device. This can thus in particular achieve the aligning of the first receiving device and the second receiving device, or the respective connecting elements received therein respectively, with one another, in particular such that the first axis of the first connecting element coincides with the second axis of the second connecting element and the first axis of the first connecting element and the second axis of the second connecting element thereby preferably coincides with the screwing axis.

Such an alignment is a prerequisite for securely and repeatably producing a threaded connection and/or for securely and in particular damage-free disengaging of a threaded connection. The apparatus, in particular the first receiving device and the second receiving device, can thereby either be designed such that the first receiving device and the second receiving device are always accordingly aligned with one another such that as soon as the first connecting element is introduced into the first receiving device and the second connecting element introduced into the second receiving device, this effects the first connecting element and the second connecting element being arranged and aligned with one another and the first axis of the first connecting element and the second axis of the second connecting element respectively coinciding and, in particular, coinciding with the screwing axis.

If this is not the case, an inventive apparatus is preferably designed such that prior to the first connecting element actually being screwed to the second connecting element, or prior to disengaging the threaded connection respectively, the first receiving device and the second receiving device can be accordingly aligned with one another such that the first connecting element and the second connecting element are aligned with each other as described above prior to the actual screwing or disengaging of the threaded connection respectively.

In a further advantageous configuration of an inventive apparatus, one of the two receiving devices, in particular the first receiving device, is arranged in position-fixed manner and the other receiving device, in particular the second receiving device, is axially displaceable along the screwing axis and rotatable about said screwing axis. A particularly simple apparatus can thus be provided, since only the second receiving device needs to be accordingly displaceably supported and only the motion of the second receiving device needs to be controlled and/or regulated.

Preferably, at least one receiving device, in particular the first receiving device, is thereby designed as a fixed clamping, while the other receiving device can preferably move translationally at least along the screwing axis and is rotatable about the screwing axis.

Preferably, in particular for automated producing and/or disengaging of a threaded connection, an inventive apparatus comprises an actuator device for generating the relative movement between the first receiving device and the second receiving device.

In a further advantageous configuration of an inventive apparatus, the apparatus comprises a spindle drive having a threaded spindle which can be driven by a drive motor for generating the relative movement between the first receiving device and the second receiving device, wherein the threaded spindle is preferably guided by means of at least one fixedly disposed bearing. The spindle drive thereby preferably comprises a first drive motor and a threaded spindle which can be driven by the first drive motor and is rotatable about the screwing axis.

If the threaded spindle is thereby of self-locking design, rotational motion of the threaded spindle around the screwing axis can preferably be effected, whereby the drive motor is or can be preferably rotationally connected to the threaded spindle to that end, if need be with a transmission gear in between, wherein the drive motor is preferably designed to rotate the threaded spindle around the screwing axis.

If, in contrast, the threaded spindle is not of self-locking design, the drive motor is preferably designed to apply an axial force on the threaded spindle, preferably by means of a rack-and-pinion gear or hydraulically or pneumatically, whereby in the case of a rack-and-pinion gear, the drive motor is preferably rotationally connected or connectable to a pinion of a rack-and-pinion gear and the rack is operatively connected to the threaded spindle and can in particular be moved toward the screwing axis such that a linear movement of the rack along the screwing axis, effectable via the pinion by the drive motor, can effect an axial movement of the threaded spindle along the screwing axis.

Due to the non-self-locking design of the threaded spindle, the axial movement in this case results in a rotational movement of the threaded spindle and, as a result, in particular to an axial displacement of the threaded spindle along the screwing axis.

The threaded spindle thereby preferably exhibits an external thread and the at least one fixedly disposed bearing is in particular, at least in part, a correspondingly designed internal thread. Due to the stationary arrangement of the bearing, the axial movement of the threaded spindle generated via the drive motor in the case of a non-self-locking spindle drive results in a rotational movement of the threaded spindle around the screwing axis.

If, however, the threaded spindle and/or the spindle drive is of self-locking design, or guided in the fixedly disposed bearing in a self-locking manner respectively, an axial force applied on the threaded spindle is borne by the fixedly disposed bearing due to the self-locking. In this case, an axial movement of the threaded spindle can only be effected by a rotation of the threaded spindle around the screwing axis such that for a threaded spindle of self-locking design, the threaded spindle is preferably rotatable about the screwing axis by means of the drive motor.

In a further advantageous configuration of an inventive apparatus, the first receiving device or the second receiving device, in particular the second receiving device, is rotationally connected or connectable to the threaded spindle, whereby the receiving device is preferably arranged in a radial recess of the threaded spindle or formed by a radial recess in the threaded spindle. The relative motion between the first receiving device and the second receiving device required to produce and/or disengage the threaded connection can thus be generated in particularly simple manner.

Preferably, only one of the receiving devices is thereby rotationally connected or connectable to the threaded spindle, or formed by a radial recess in the threaded spindle or arranged in a radial recess of the threaded spindle respectively. However, each of the two receiving devices can be rotationally connected or connectable to a threaded spindle and preferably arranged in a radial recess of the threaded spindle or formed by a radial recess in the threaded spindle. Doing so yields a particularly simple way of both receiving devices being able to be moved separately from each other.

Particularly preferential, however, is for one of the two receiving devices to be of stationary design, in particular the first receiving device, and only the second receiving device to be rotationally connected or connectable to a threaded spindle and preferably arranged in a radial recess of the threaded spindle or formed by a radial recess in the threaded spindle.

In an alternative configuration of an inventive apparatus, the apparatus comprises a first drive motor and a gear mechanism having a first gear element and at least one second gear element rotationally connected to the first gear element which can be driven by means of the first drive motor for generating the relative movement between the first receiving device and the second receiving device, wherein the first receiving device or the second receiving device, in particular the second receiving device, is rotationally connected or connectable to the first gear element. A relative motion between the first receiving device and the second receiving device can in this way likewise be effected in particularly simple manner.

Preferably, the gear mechanism is thereby a pinion gear, in particular a spur gear, wherein the gear mechanism is in particular rotationally connected or connectable to the drive motor. Alternatively, the gear mechanism can also be a belt drive having at least two pulleys operatively connected together by a belt or a friction gear having at least two friction wheels operatively connected together by friction.

If the gear mechanism is designed as a pinion gear, the first gear element is preferably a gearwheel and the second gear element is a gearwheel, wherein the second gearwheel preferably meshes with the first gearwheel. Particularly preferentially, the gear mechanism can thereby be driven via the first drive motor, in particular by means of the second gear element.

In a further advantageous configuration of an inventive apparatus, the first receiving device or the second receiving device, in particular the second receiving device, is arranged in a radial recess of the first gear element or formed by a radial recess in the first gear element. The first receiving device can thus be rotated around the screwing axis in particularly simple manner in order to produce and/or disengage the threaded connection.

In some cases, in particular if an angle of rotation of greater than 360° minus the opening angle of the recess in the first gear element is necessary for screwing, an inventive apparatus comprises a third gear element rotationally connected or connectable to the first gear element, whereby the third gear element can preferably be driven by means of the first drive motor and/or by means of a further drive motor. The first gear element can thereby be driven by means of the third gear element in the angular range in which the first gear element cannot be driven by means of the second gear element due to its radial recess and thus the third gear element is able to bridge the angular range which the second gear element is unable to utilize for the drive due to the recess in the first gear element.

This can particularly be necessary when a relative rotation of more than 360° about the screwing axis between the first connecting element and the second connecting element minus the opening angle of the recess in the first gear element is needed to produce a secure threaded connection, which in particular can be the case when at least one of the connecting elements cannot be repeatably inserted in the circumferential direction such that the angle of rotation required to produce the threaded connection and/or disengage the threaded connection fluctuate sharply.

In a further advantageous configuration of an inventive apparatus, the apparatus is designed to push the first receiving device and the second receiving device together along the screwing axis, in particular press them together, and/or pull them apart. To this end, the apparatus, in particular the actuator device of an inventive apparatus, comprises an axial force generating device. This is in particular advantageous, or in some cases even necessary, when the apparatus does not have a spindle drive but only a conventional gear mechanism driven via a drive motor for generating the relative movement between the first receiving device and the second receiving device.

A spring-loaded system, in particular comprising at least one helical spring for generating the necessary axial force, is particularly suited as an axial force generating device, wherein the spring is preferably arranged such that an axial force is generated in the desired direction; i.e. in particular to push and/or press the first receiving device and the second receiving device together and/or pull them apart, wherein it can be advantageous in some cases for the apparatus to additionally comprise a locking device, by means of which the first receiving device and/or the second receiving device can be locked in the axial direction against the axial force produced by means of the spring.

In a further alternative configuration of an inventive apparatus, the first receiving device and/or the second receiving device, in particular the second receiving device, is/are mounted on a gripper arm, whereby the gripper arm is preferably displaceable at least along the screwing axis and, in particular, rotatable about the screwing axis. Particularly preferentially, the first receiving device and/or the second receiving device, in particular the second receiving device, is/are formed by a gripper.

In a further alternative configuration of an inventive apparatus, the apparatus is designed such that the first connecting element and the second connecting element of the threaded connection can respectively be removed radially from the first receiving device and the second receiving device after the threaded connection having been made. To this end, preferably both receiving devices have a respective recess outwardly opened in the radial direction designed to receive the associated connecting element or a respective gripper.

The radial recess of the first receiving device is thereby situated in a first defined circumferential angular range and the recess of the second receiving device in a second angular range, in particular after the threaded connection having been made, wherein the first angular range and the second angular range at least partially overlap. An apparatus designed in this way enables a particularly simple removal and/or discarding of a threaded connection produced by means of the inventive apparatus.

In particular, an inventive apparatus designed in this way enables the particularly quick and easy automated producing of threaded connections having a tube element, in particular medical Luer lock threaded connections having at least one tube. In particular, all external fluid system tube connections can be produced in automated and extremely efficient manner, and thus repeatably and secure, with an inventive apparatus.

The angular range in which the radial recesses of the first receiving device and the second receiving device are preferably situated after the threaded connection is made is thereby in particular selected such that the threaded connection produced, if desired, drops due to the force of gravity or in fact does not drop by the force of gravity and is securely held in the apparatus until removal.

In a further advantageous configuration of an inventive apparatus, the apparatus is designed such that when screwed together, the first connecting element and the second connecting element of the threaded connection can respectively be radially introduced into the first receiving device and the second receiving device to disengage the threaded connection. To that end, preferably both receiving devices have a respective recess outwardly opened in the radial direction designed to receive the associated connecting element or a respective gripper, whereby the radial recess of the first receiving device is situated in a first defined circumferential angular range and the radial recess of the second receiving device in a second angular range, in particular prior to the threaded connection being disengaged, wherein the first angular range and the second angular range at least partially overlap. Thus, in particularly easy and thus efficient manner, a threaded connection by means of which two tubes are connected together can be introduced particularly inventively into the apparatus radially such that the threaded connection does not have to be circuitously introduced into the apparatus axially because of the tubes.

In a further advantageous configuration of an inventive apparatus, the apparatus can be operated in two operating modes, in particular a first operating mode for producing the threaded connection and a second operating mode for disengaging the threaded connection. This allows particularly easily ensuring that the receiving devices are respectively oriented to produce a threaded connection such that after the threaded connection is produced, the threaded connection can be removed in the radial direction, whereby to that end, after the respective operating mode has been activated, preferably prior to the screwing of the two connecting elements together, particularly preferentially prior to the introduction of the two connecting elements, the receiving devices of the apparatus are aligned such that, after the two connecting elements are screwed together, they are respectively arranged relative to each other so as to allow the threaded connection to be radially removed from the apparatus as described above.

For disengaging the threaded connection, the two receiving devices are preferably in an orientation prior to the threaded connection being introduced such that the threaded connection can be, as described, introduced radially into the apparatus.

A method according to the invention for producing and/or disengaging a fluid flow-capable medical threaded connection of a first connecting element and a second connecting element, preferably producing and/or disengaging a Luer lock connection, by means of an apparatus comprising a first receiving device and a second receiving device, wherein the first receiving device and the second receiving device are rotatable relative to each other about a common screwing axis and displaceable relative to each other along said screwing axis, in particular by means of an apparatus designed in accordance with the claims, comprising the following steps:

Providing a first connecting element and a second connecting element to be connected to the first connecting element or the threaded connection to be disengaged, Introducing the first connecting element into the first receiving device of the apparatus, Introducing the second connecting element into the second receiving device of the apparatus, Moving the first receiving device relative to the second receiving device such that the first connecting element and the second connecting element screw together or the threaded connection disengages.

A method according to the invention is thereby characterized in that the first connecting element and/or the second connecting element, or the threaded connection, is/are introduced into the associated receiving device in the radial direction in relation to the screwing axis.

Preferably, to produce the threaded connection, the second receiving device can be displaced along the screwing axis, in particular pushed together along with the first receiving device, and rotated around the screwing axis, in particular while simultaneously under an externally originating axial force.

To disengage the threaded connection, the second receiving device can be preferably displaced along the screwing axis away from the first receiving device and thereby simultaneously around about the screwing axis, preferably likewise under axial force load, albeit with opposite direction of application. Preferably, at least the movement of the two receiving devices relative to each other is thereby automated, preferably controlled, in particular regulated, wherein it is particularly preferential for the relative movement of the first receiving device to the second receiving device to ensue in torque-controlled or torque-regulated and/or force-controlled or force-regulated and/or rotation angle-controlled or rotation angle-regulated and/or path-controlled or path-regulated manner.

Preferably, the first connecting element and/or the second connecting element is/are additionally introduced automatically into the respectively associated receiving device. In some cases, it can be also advantageous for the providing of the first connecting element and/or the second connecting element to likewise be automated.

Should an apparatus used to implement an inventive method, in particular its first receiving device and/or its second receiving device, thereby not be designed and arranged so that the respectively associated connecting elements are aligned with each other after introduction into the associated receiving device such that the first axis of the first connecting element and the second axis of the second connecting element coincide, particularly with the screwing axis, the first receiving device and the second receiving device are preferably first moved relative to one another such that this then subsequently becomes the case; i.e. after aligning. This thereby enables the near-optimal arrangement of the first connecting element and the second connecting element for producing the threaded connection or disengaging the threaded connection.

In one advantageous configuration of an inventive method, after the threaded connection has been made, the first connecting element and the second connecting element of the threaded connection are in each case removed from the first receiving device and the second receiving device in the radial direction, in particular in the same radial direction.

After disengaging of the threaded connection, one advantageous implementation of an inventive method provides for preferably removing at least one connecting element in the radial direction, in particular both connecting elements are preferably removed in the radial direction. However in this case, the two connecting elements can also be removed in differing radial directions without any problem.

In a further advantageous configuration of an inventive method, a first operating mode is activated to produce the threaded connection, particularly prior to the introduction of the first connecting element and/or the second connecting element, and/or a second operating mode is activated to disengage the threaded connection, in particular prior to the introduction of the threaded connection. The apparatus can thereby be particularly easily brought into an optimal position in each case for the introduction of the two connecting elements.

Further conceivable preferential configurations of the method according to the invention can be deduced from the description of the inventive system and its preferential configurations.

The advantageous configurations and their specific advantages presented with respect to an inventive apparatus for producing and/or disengaging a fluid flow-capable medical threaded connection also apply analogously to an inventive method for such a threaded connection.

The present invention also relates to a cannulation robot comprising an inventive apparatus (100, 200, 200', 300) in accordance with at least one of the possible configurations described herein for producing and/or disengaging a fluid flow-capable medical threaded connection and which is in particular designed to implement an inventive method. The cannulation robot is thereby in particular designed to automatically and autonomously establish medical fluid connections, in particular Luer lock connections, in particular subsequent to the cannulation robot having previously effected automated cannulation of the patient's blood vessel and in particular subsequent to the cannulation robot automatically fixing the venipuncture cannula on the patient's skin with adhesive tape or by other fixing device.

A cannulation robot is an apparatus which automatically; i.e. intermittently or continuously, performs at least one cannulation process step in a patient blood vessel, or several or all intended process steps, without the intervention of a human operator, e.g. medical personnel. This process step is in particular the automatic puncturing of the blood vessel, in particular an arteriovenous fistula; preferably a first venipuncture and cannulation occurring automatically for withdrawing blood from the blood vessel and a second venipuncture and cannulation occurring automatically for the return of the blood, in particular in the case of hemodialysis; the program parameters of the automated cannulation can hereby be selected as a function of the registered patient identifier, thus individual to the specific patient, by the program parameters defining a patient-dependent motion control for a robotic tool arm optionally provided in the cannulation robot, by means of which medical equipment such as for instance an injection needle can for example be grasped by the tool arm and positioned on the body part, with the injection needle having been previously selected and prepared specific to the patient; two cannulation robots can be set up for venipuncturing blood vessels at different parts of the body by, for example, a first cannulation robot being configured for cannulation on an arm and a second cannulation robot being configured for cannulation on a leg; the selection of the appropriate cannulation robot can ensue in patient-specific and/or treatment-specific manner.

Further preferential configurations of the system according to the invention and the method according to the invention are yielded by the following description of example embodiments in conjunction with the figures and their description. Unless expressly specified or contextually indicated otherwise, the same reference numerals are substantially used to identify equivalent components in the example embodiments.

Figure 1B:
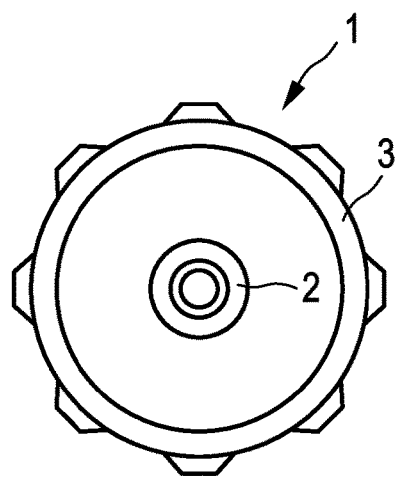
Figure 1C:
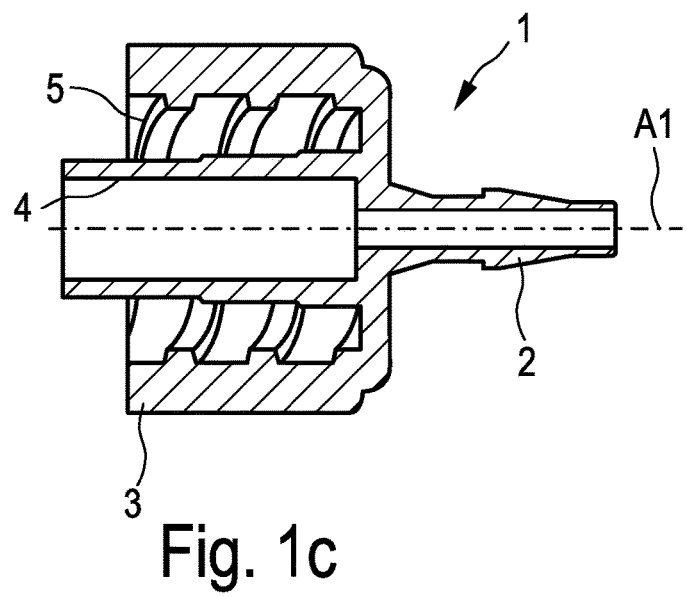
Figure 2A:
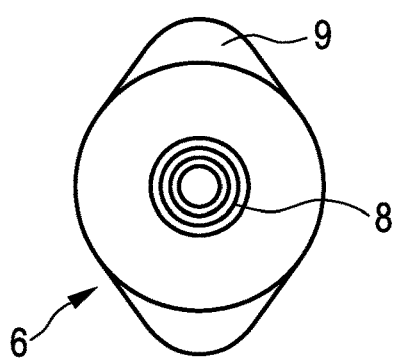
Figure 2B:
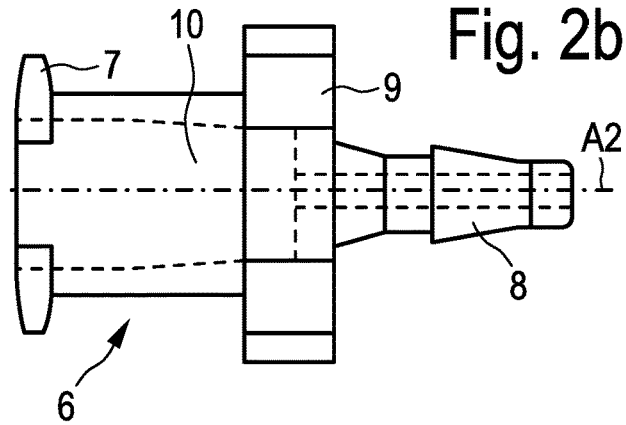
Figure 2C:
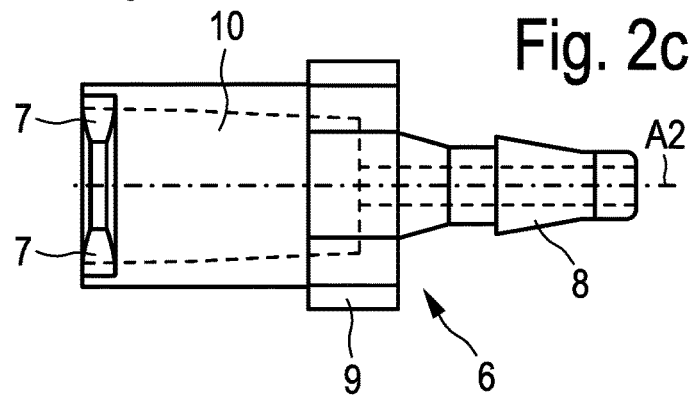
Figure 3A:
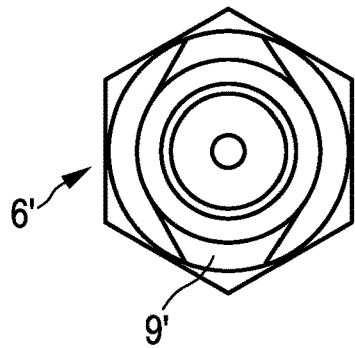
Figure 3B:
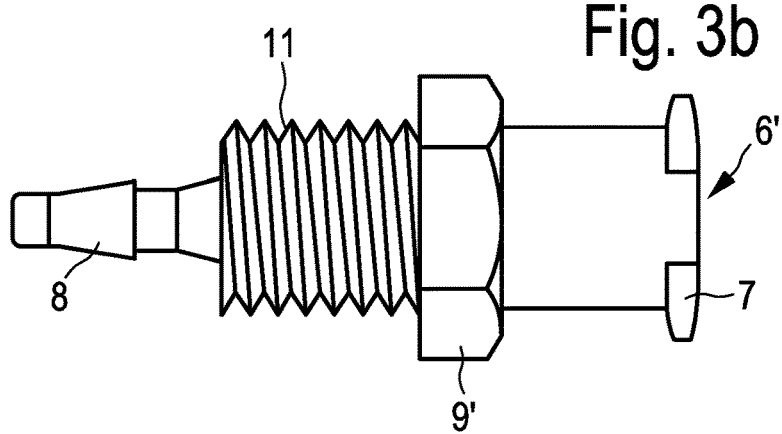
Figure 3C:
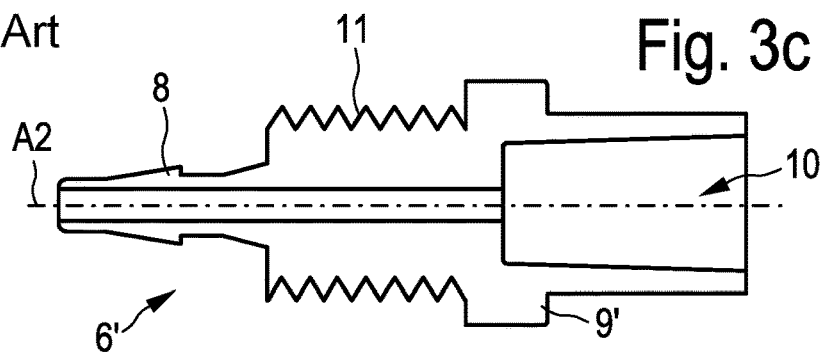
Figure 4:
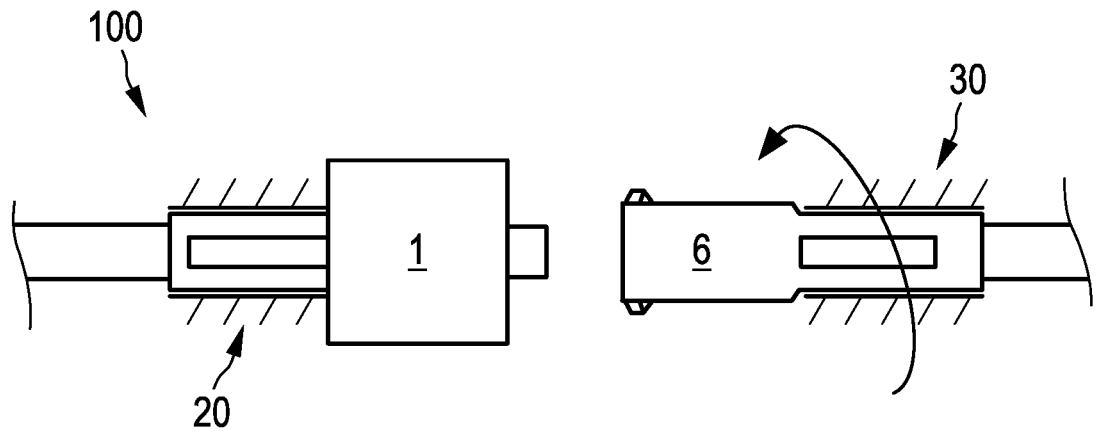
Figure 5:
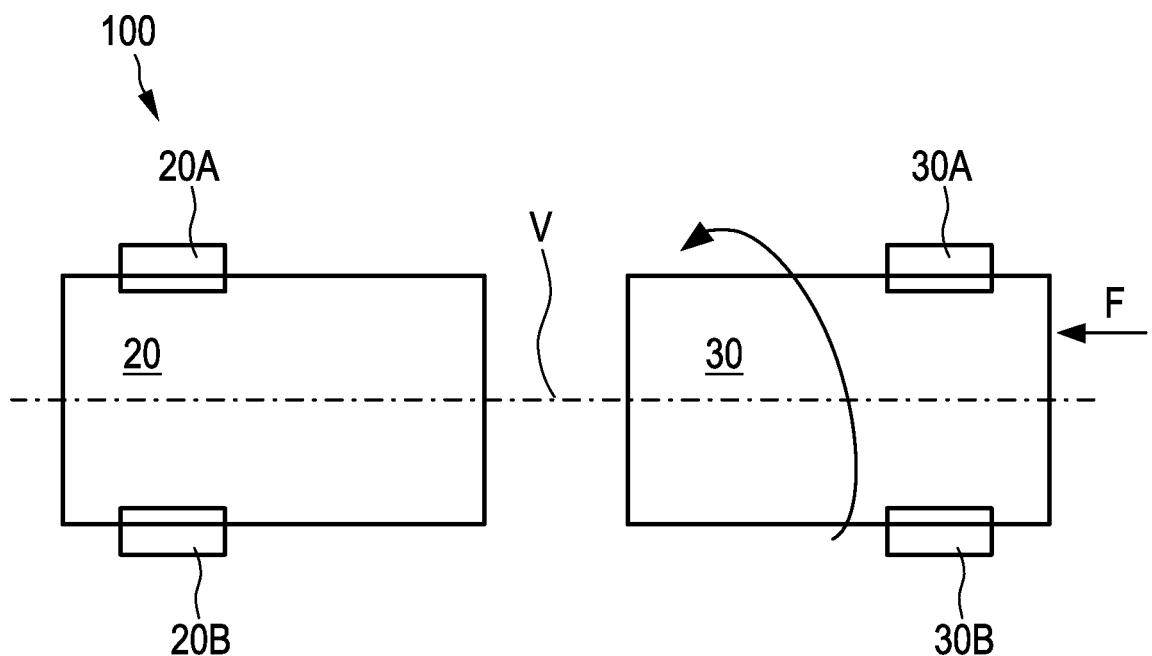
Figure 6A:
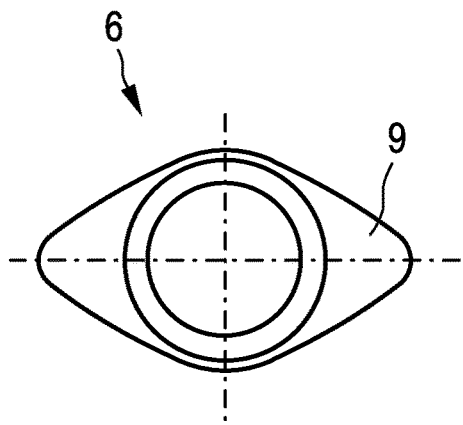
Figure 6B:
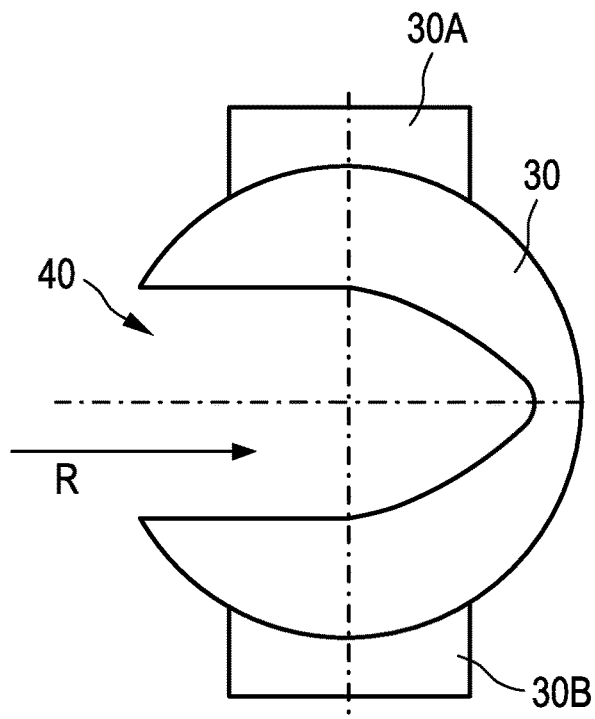
Figure 6C:
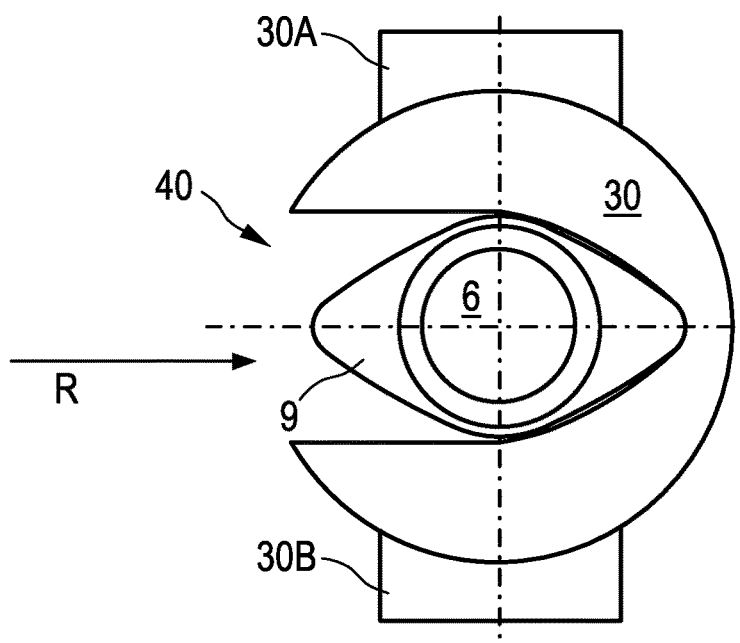
Figure 9:
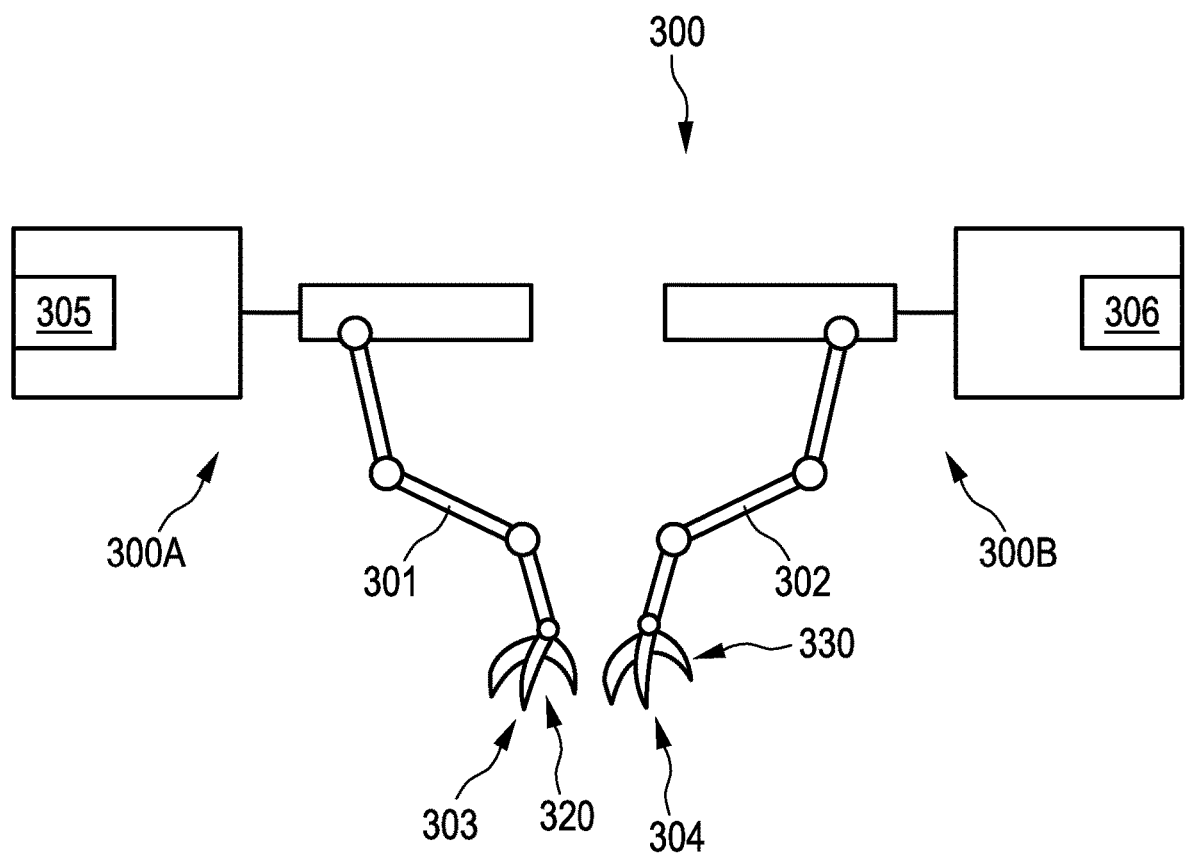

Shown are:

FIG. 1a to 1c: different schematic views of a first example embodiment of a Luer lock connector known from the prior art having a male Luer lock connecting section, FIGS. 2a to 2c: different schematic views of a first example embodiment of a Luer lock connector known from the prior art having a female Luer lock connecting section, FIGS. 3a to 3c: different schematic views of a second example embodiment of a Luer lock connector known from the prior art having a female Luer lock connecting section, FIG. 4: a schematic view from above of a first example embodiment of an apparatus according to the invention for producing a threaded Luer lock connection, FIG. 5: a schematic diagram from the front of the inventive apparatus of FIG. 4, FIG. 6a: the Luer lock connector from FIG. 2a prior to introduction into the second receiving device of the inventive apparatus from FIGS. 4 and 5, FIG. 6b: a schematic diagram of the inventive apparatus from FIGS. 4 and 5 from the side prior to introduction of the Luer lock connector from FIG. 6a into the second receiving device, FIG. 6c: a schematic diagram of the inventive apparatus from FIGS. 4 and 5 from the front after the introduction of the Luer lock connector from FIG. 6a into the second receiving device, although prior to producing the threaded Luer lock connection, FIG. 7: a schematic side view of a second example embodiment of an inventive apparatus for producing a threaded Luer lock connection subsequent the introduction of the Luer lock connector from FIG. 2a into the second receiving device, although prior to producing the threaded Luer lock connection, FIG. 8a: a schematic side view of a third example embodiment of an inventive apparatus for producing a threaded Luer lock connection in a first state prior to the introduction of a Luer lock connector into the second receiving device, FIG. 8b: the apparatus from FIG. 8a in a second state, and FIG. 9: a schematic side view of a fourth example embodiment for producing a threaded Luer lock connection.

FIGS. 1a to 1c in each case show a schematic view of a first example embodiment of a Luer lock connector 1 known from the prior art having a male Luer lock connecting section 5, whereby FIG. 1a shows a Luer lock connector from the side, FIG. 1b shows a view from the rear, and FIG. 1c shows a sectional view.

The Luer lock connector 1 thereby comprises a tube connecting section 2 as well as a sleeve-shaped male Luer lock connecting section 3 having an internal threading 5 arranged concentrically to a tube section 4 around a first axis A1. The tube section 4 thereby comprises, as is common with Luer connectors, an external taper of 6% angle of slope and through which a fluid medium can flow just as with tube connecting section 2. The sleeve-shaped male Luer lock connecting section 3 exhibits a plurality of circumferentially distributed ribs (not further specified here) on its exterior.

FIGS. 2a to 2c in each case show a schematic view of a first example embodiment of a Luer lock connector 6 known from the prior art having a female Luer lock connecting section 10, whereby FIG. 2a shows a view from the rear, FIG. 2b shows a view from above, and FIG. 2c shows a side view.

The Luer lock connector 6 thereby has a female Luer lock connecting section 10 formed as an internal taper which likewise has a 6% angle of slope. The Luer lock connector 6 likewise comprises a tube connecting section 8. A fluid medium can likewise flow through the internal taper 10 as well as the tube connecting section 8.

To connect the female Luer lock connector 6 to a male Luer lock connector 1, as is depicted in the example of FIGS. 1a to 1c, the Luer lock connector 6 depicted in FIGS. 2a to 2c comprises a flange section extending outwardly in the radial direction and having an external thread 7, wherein the external thread 7 as well as the internal taper 10 are arranged concentric to a second axis A2 of the connecting element 6.

To make manipulation of the female Luer lock connector 6 particularly easy, same has in this case a handling profile 9 in the form of two wings at the approximate center relative to its longitudinal extension toward the second axis A2, each exhibiting the approximate geometry of a half-rhombus with rounded corners. Female Luer lock connectors 6 having such handling profiles 9 are generally known in the prior art such that no further remarks will be made thereto at this point.

FIGS. 3a to 3c in each case schematically depict, likewise in different views, a second example embodiment of a Luer lock connector 6' known from the prior art likewise comprising a female Luer lock connecting section 10.

This Luer lock connector 6' thereby differs in its handling profile 9' as well as in an additional connecting thread 11 arranged adjacent to the tube connecting section 8 and the handling profile 9', in particular between the tube connecting section 8 and the handling profile 9'.

Otherwise, the female Luer lock connector depicted in FIGS. 3a to 3c is of similar design to the Luer lock connector 6 described on the basis of FIGS. 2a to 2c. In particular, the female connecting section 10 with the conical internal taper and external thread 7 is of identical design to the Luer lock connector 6 of FIGS. 2a to 2c, as also stipulated by the respective Luer lock connector standards, which only permit differing sizes however stipulate the individual dimensions being at a specific ratio to one another.

FIG. 4 shows a schematic view from above of a first example embodiment of an inventive apparatus 100 for producing a Luer lock threaded connection, wherein the inventive apparatus 100 comprises a first receiving device 20 as well as a second receiving device 30.

The first receiving device 20 is in this case designed as a fixed clamping and for receiving a first connecting element 1, which is represented as an example here as the known prior art male Luer lock connector 1 as previously described with a male Luer lock connecting section.

The fixed clamping of the first receiving device 20 is effected by an upper bearing shell 20A as well as by a lower bearing shell 20B with which the first receiving device is arranged in stationary manner within the inventive apparatus 100, see FIG. 5.

The second receiving device 30 is designed to receive a second connecting element which is represented as an example here as the known prior art second Luer lock connector 6 as previously described with a female Luer lock connecting section.

The second receiving device 30 is thereby formed by a threaded spindle which is symbolized by the direction of arrow and which is rotatable about a screwing axis (not further specified here) and axially displaceable along the screwing axis.

The second receiving device 30 thereby has a (not-shown) non-self-locking external thread which engages with a correspondingly configured likewise not shown internal thread of an upper bearing shell 30A and lower bearing shell 30B and enables axial guidance of the threaded spindle 30 along the screwing axis V.

For sufficiently accurate guidance of the threaded spindle 30 or sufficiently stable supporting of the first receiving device 20 respectively, it can in some cases be necessary for more than one bearing along with the correspondingly designed bearing shells 20A, 20B, 30A and 30B to be provided.

Due to the non-self-locking configuration of the threaded spindle 30, a rotational movement around the screwing axis V can be induced by an axial force F being applied on the threaded spindle, whereby the threaded spindle 30 is displaced along the screwing axis V in the axial direction as a result of the rotational motion.

To screw the first connecting element 1 and the second connecting element 6 together, the second receiving device 30 can be axially displaced along the screwing axis V, in particular by the applying of a sufficient axial force F.

The axial force F can thereby be generated preferably by means of an accordingly designed actuator device (not depicted here), e.g. with a drive motor and a rack-and-pinion gear, wherein preferably a pinion of the rack-and-pinion gear is non-rotatably connected to the drive motor and can be set into rotation by means of the drive motor, whereby a rack meshing with the pinion can be axially displaced, this being able to be utilized to apply an axial force on the threaded spindle 30.

If, however, the threaded spindle 30 is of self-locking design or, respectively, the spindle drive is comprised of the threaded spindle 30 and the associated bearing shells 30A and 30B guiding the threaded spindle, it is not possible to induce an axial movement of the threaded spindle 30 by applying an axial force F since in this case, axial forces applied on the threaded spindle 30 are borne by the bearing shells 30A and 30B. In this case, a rotational movement of the threaded spindle can only be effected by rotation of the threaded spindle 30, whereby the required axial movement to screw the two connecting elements 1 and 6 together can in this case be produced.

In this inventive apparatus 100, the first receiving device 20 and the second receiving device 30 are arranged and designed with respect to one another so that the respectively associated Luer lock connectors 1 and 6 can be respectively accommodated such that a first axis A1 of the first connecting element 1 and a second axis A2 of the second connecting element 6 align with each other directly after being introduced into the apparatus 100 and, in particular, coincide with the screwing axis V so that the first connecting element 1 and the second connecting element 6 can be screwed together immediately following introduction.

As a result of the non-self-locking threaded spindle 30, the applied axial force F causes a rotational movement of the threaded spindle 30 about the screwing axis V, whereby the second receiving device 30, which is formed by a radial recess 40 in the threaded spindle 30, is simultaneously rotated around the screwing axis V. The rotating motion of the threaded spindle 30 in turn induces its axial movement toward the first receiving device 20.

Thus, if the rotational movement about the screwing axis V extends over a sufficiently large angle of rotation or is rendered over a sufficiently large angle of rotation respectively, a second connecting element 6 accommodated in the second receiving device 30 can be screwed to a first connecting element 1 accommodated in the second receiving device 20 in particularly simple manner, particularly automated, and a threaded connection produced.

Correspondingly, applying an opposite axial force can effect a rotational movement of the second receiving device 30 in the opposite direction with simultaneous axial displacement of the threaded spindle 30 away from the first receiving device 20, by means of which a threaded connection can be disengaged.

FIG. 6a shows the connecting element 6 from FIG. 2a in an exploded view prior to the introduction of the second receiving device 30 of the inventive apparatus 100 from FIGS. 4 and 5.

FIG. 6b shows a schematic diagram of the inventive apparatus 100 from FIGS. 4 and 5 in a view from the side prior to the connecting element 6 from FIG. 6a being introduced into the second receiving device 30.

It can be easily seen from this depiction that the second receiving device 30 comprises a recess 40 outwardly open in the radial direction R designed to receive the second connecting element 6 which is at least partly adapted in particular to the handling profile 9 of the second connecting element 6. Thus, not only the second connecting element 6 can thereby be received by the second receiving device 40 in particularly simple manner but also form-fit secured against rotation about the (not further identified here) screwing axis V which, in this depiction, extends perpendicular to the plane of projection. This is easily discernible from FIG. 6c, which shows the inventive apparatus 100 from FIGS. 4 and 5 as well as 6b after the Luer lock connector 6 having been introduced into the second receiving device 30 however prior to the Luer lock threaded connection being made.

FIG. 7 shows a schematic side view of a second example embodiment of an inventive apparatus 200 for producing and disengaging a Luer lock threaded connection subsequent the Luer lock connector 6 from FIG. 2a having been introduced into the second receiving device 30 however prior to the Luer lock threaded connection being made.

In this case, the second receiving device 130 is formed by a first gear element 130 in the form of a straight-cut spur wheel 130 which engages by means of a second gear element 31, likewise formed as a straight-cut spur wheel 31 and which is rotationally connected to a first drive motor and can be set into a rotational motion via same.

To generate the relative axial movement between the (not shown here) first receiving device and the second receiving device (130) also required to produce the threaded connection in addition to the rotational movement, the inventive apparatus 200 comprises a (not shown here) spring tensioning system, or spring tensioning apparatus respectively, designed to axially displace the connecting device 130 toward the first receiving device such that the second connecting element 6 can be screwed to the associated, correspondingly configured other connecting element 1, which is accommodated by the first receiving device, into a threaded connection.

A clockwise rotational movement of the second spur wheel 31 thereby results in a counterclockwise rotational movement of the first spur wheel 130 and thus the first receiving device 130 formed by the radial recess 40 in the first gear element 31.

As with the previously described inventive apparatus 100, the recess 40 is also formed in this case in correspondence with the handling profile 9 of the second connecting element 6 and in particular designed such that the second connecting element 6 can be disposed rotationally fixed in the second receiving device 130.

If the angle of rotation required to produce the threaded connection is thereby greater than the area formed in the circumferential direction of the first gear element 130 with external teeth; i.e. greater than 360° minus the angle of rotation of recess 40, the threaded connection cannot be properly screwed together by means of the inventive apparatus 200 depicted in FIG. 7 since no drive by means of the second gear element 31 is possible in the area of the recess 40, particularly if the angular range in the area of the opening 40 is thereby so great that the second gear element 31 at least partly disengages.

The inventive apparatus 200' depicted in FIGS. 8a and 8b lends itself in particular to this specific case, which in addition to the first gear element 130, which forms the second receiving device 130 and respectively comprises a radial recess 40 as with the two previously described inventive apparatus 100 and 200, also comprises a second gear element 32 and even a third gear element 34, likewise rotationally connected to the first gear element 130 and, in particular, likewise engaging/meshing with the first gear element 130.

In this case, the second gear element 32 and the third gear element 34 are operatively connected by way of a further fourth gear element 33 so that drive power applied by a first drive motor on the second gear element 32 can on the one hand be transmitted to the first gear element 31 by the second gear element 32 and, on the other hand, also transmitted to the first gear element 31 by the fourth gear element 33 and the third gear element 34.

In particular, if the recess 40 is situated in the area of the second gear element 32, as depicted in FIG. 8b for better understanding, the fourth gear element 33 and the third gear element 34 can transmit drive power generated by a drive motor to the first gear element 130, thereby enabling the bridging of the non-toothed angular range in the area of recess 40.

If, as in the example embodiment of an inventive apparatus 200' illustrated by way of FIGS. 8a and 8b, only one drive motor is provided for the drive of the second gear element 32, it is necessary for the third gear element 34 to be coupled to the second gear element 32 via a fourth gear element 33 due to the required reversal of rotational direction, which is particularly apparent from the rotation arrows provided in FIG. 8b.

If the second gear element 32 namely turns in the clockwise direction, a counter-clockwise direction of rotation results for the fourth gear element 33, whereby the third gear element 34 in turn rotates clockwise just like the second gear element 32 so that blocking of the gearing can be prevented when both the second gear element 32 as well as the third gear element 34 are in engagement with the first gear element 130.

Alternatively, it is also possible to provide a second drive motor in place of the fourth gear element 33 and utilize same to drive the third gear element 34, whereby in this case, the drive power needs to be applied in the same direction of rotation as with the second gear element 33, in particular in rotational speed synchronization with the first gear element 130.

FIG. 9 shows a schematic view of a fourth example embodiment of an inventive apparatus 300 for producing and/or disengaging a Luer lock threaded connection, whereby this inventive apparatus 300 comprises a first gripper apparatus 300A and a second gripper apparatus 300B. The first gripper apparatus 300A thereby has a gripper arm 301 with a first receiving device 320 formed by a gripper 303 attached to the free end of said gripper arm 301, wherein control device 300B is provided for the controlling of the first gripper apparatus 300A.

The second gripper apparatus 300B is of analogous design to the first gripper apparatus 300A and likewise comprises a gripper arm 302 having a second receiving device 330 formed by a gripper 304 attached to its free end. Control device 306 is correspondingly provided for controlling the second gripper apparatus 300B.

A plurality of variations, in particular of a structural nature, is of course possible without departing from the content of the claims.

LIST OF REFERENCE NUMERALS

1 Luer lock connector with male Luer lock connecting section
2 tube connecting section
3 sleeve-shaped male Luer lock connecting section with internal thread
4 tube section with external taper
5 internal thread
6, 6' Luer lock connector with female Luer lock connecting section
7 external thread
8 tube connecting section
9, 9' handling profile
10 female Luer lock connecting section with internal taper
11 connecting thread
20 first receiving device
20A upper bearing shell of first receiving device
20B lower bearing shell of first receiving device
30 second receiving device, threaded spindle
30A upper bearing shell of second receiving device
30B lower bearing shell of second receiving device
31 second gear element
32 second gear element
33 fourth gear element
34 third gear element
40 recess
100, 200, 200', 300 inventive apparatus
130 second receiving device; first gear element
300A first gripper apparatus
300B second gripper apparatus
301 gripper arm of first gripper apparatus
302 gripper arm of second gripper apparatus
303 gripper of first receiving device
304 gripper of second receiving device 305 control device for controlling the first gripper apparatus
306 control device for controlling the second gripper apparatus
320 first receiving device
330 second receiving device
A1 first axis
A2 second axis
F axial force
R radial direction
V screwing axis

The invention claimed is:

1. An apparatus for producing and/or disengaging a fluid flow-capable medical threaded connection of a first connecting element and a second connecting element, the apparatus comprising a first receiving device for receiving the first connecting element and a second receiving device for receiving the second connecting element, wherein
the first receiving device and the second receiving device are rotatable relative to each other about a common screwing axis and displaceable relative to each other along the screwing axis,
the apparatus is designed to relatively move the first receiving device and the second receiving device toward or away from each other after introduction of the first connecting element into the first receiving device and introduction of the second connecting element into the second receiving device, such that the first connecting element and the second connecting element are screwed together or a threaded connection between the first connecting element and the second connecting element is disengaged,
the respective connecting element is introduced into the respective first receiving device and/or the second receiving device in a radial direction relative to the screwing axis,
the apparatus comprises a spindle drive having a threaded spindle that is configured to be driven by a drive motor for generating the relative movement between the first receiving device and the second receiving device, wherein the threaded spindle is guided by means of at least one fixedly disposed bearing,
the first receiving device or the second receiving device is rotationally connected or connectable to the threaded spindle and arranged in a radial recess of the threaded spindle or formed by a radial recess in the threaded spindle.

2. The apparatus according to claim 1, wherein the apparatus is designed to at least semi-automatically produce and/or disengage the threaded connection.

3. The apparatus according to claim 1, wherein one of the two receiving devices is designed for receiving a first connecting element comprising a first connecting section having a sleeve-shaped internal thread arranged concentric to a first axis, with a male Luer lock connecting section, and the other receiving device is designed for receiving a second connecting element comprising a second connecting section having an external thread arranged concentric to a second axis with a female Luer lock connecting section.

4. The apparatus according to claim 1, wherein one of the two receiving devices is arranged in a position-fixed manner and the other receiving device is axially displaceable along the screwing axis and rotatable about said screwing axis.

5. The apparatus according to claim 1, wherein the apparatus comprises a first drive motor and a gear mechanism, the gear mechanism having a first gear element and at least one second gear element rotationally connected to the first gear element, and is configured to be driven by means of the first drive motor, for generating the relative movement between the first receiving device and the second receiving device, and the first receiving device or the second receiving device is rotationally connected or connectable to the first gear element.

6. The apparatus according to claim 5, wherein the apparatus is designed to push the first receiving device and the second receiving device together along the screwing axis and/or pull them apart.

7. The apparatus according to claim 1, wherein the first receiving device and/or the second receiving device is/are mounted on a gripper arm.

8. The apparatus according to claim 1, wherein the apparatus is designed such that the first connecting element and the second connecting element of the threaded connection can be removed from the first receiving device and the second receiving device in the radial direction after the threaded connection between the first connecting element and the second connecting element has been made.

9. The apparatus of claim 1, wherein the fluid flow-capable medical threaded connection is a Luer lock connection.

10. A method for producing and/or disengaging a fluid flow-capable medical threaded connection of a first connecting element and a second connecting element by means of an apparatus according to claim 1, comprising the steps:
providing a first connecting element and a second connecting element to be connected to the first connecting element or the threaded connection to be disengaged,
introducing the first connecting element into the first receiving device of the apparatus,
introducing the second connecting element into the second receiving device of the apparatus, and
moving the first receiving device relative to the second receiving device such that the first connecting element and the second connecting element screw together or the threaded connection disengages, wherein
the first receiving device and/or the second receiving device comprises a gripper or is designed as a gripper, and
the first connecting element and/or the second connecting element, or the threaded connection, is/are introduced into one or both respective receiving devices in the radial direction relative to the screwing axis.

11. The method according to claim 10, wherein after the threaded connection has been made, the first connecting element and the second connecting element of the threaded connection are removed from the first receiving device and the second receiving device, respectively, in the radial direction.

12. A cannulation robot comprising an apparatus in accordance with claim 1.

* * * * *